(12) United States Patent
Tominaga (10) Patent No.: US 6,507,201 B2
(45) Date of Patent: Jan. 14, 2003

(54) SYSTEM FOR MEASURING AMOUNT OF SPECIFIC SUBSTANCE MIXED IN MATERIAL UNDER MEASUREMENT AND ELECTRODE ROD FOR MEASUREMENT

(75) Inventor: Masaki Tominaga, Tsukuba (JP)

(73) Assignee: National Research Institute for Earth Science and Disaster Prevention, Tsukuba (JP)

( * ) Notice: Subject to any disclaimer, the term of this patent is extended or adjusted under 35 U.S.C. 154(b) by 0 days.

(21) Appl. No.: 09/901,043

(22) Filed: Jul. 10, 2001

(65) Prior Publication Data

US 2002/0060576 A1 May 23, 2002

(30) Foreign Application Priority Data

Jul. 13, 2000 (JP) ........................................ 2000-212083
Jul. 13, 2000 (JP) ........................................ 2000-212084

(51) Int. Cl.$^7$ .............................................. G01R 27/08
(52) U.S. Cl. ...................................................... 324/715
(58) Field of Search ................................ 324/434, 436, 324/437, 444, 700, 705, 715, 717; 204/400, 404

(56) References Cited

U.S. PATENT DOCUMENTS 3,993,945 A * 11/1976 Warmouth et al. .......... 324/308

\* cited by examiner

*Primary Examiner*—Christine Oda
*Assistant Examiner*—Etienne LeRoux
(74) *Attorney, Agent, or Firm*—Armstrong, Westerman & Hattori LLP (57) ABSTRACT

A measuring system has at least four electrodes and an electric current measuring resistance placed in a material under measurement in a desired manner. A power supply supplies an alternating current between two of the electrodes through the resistance. A current measuring unit measures an electric current flowing through the resistance. A voltage measuring unit measures an electric potential difference between electrodes other than the electrodes supplied with the alternating current. A computing unit obtains a conductivity on the basis of the measured electric current and electric potential difference, together with a coefficient determined by the manner in which the electrodes are placed, and performs conversion based on calibration data to obtain the amount of a specific substance mixed in the material under measurement.

9 Claims, 6 Drawing Sheets

SYSTEM FOR MEASURING AMOUNT OF SPECIFIC SUBSTANCE MIXED IN MATERIAL UNDER MEASUREMENT AND ELECTRODE ROD FOR MEASUREMENT

BACKGROUND OF THE INVENTION

The present invention relates to a system for measuring the amount of a specific substance mixed in a material under measurement from a measured value of conductivity of the material obtained with at least four electrodes. The present invention also relates to an electrode rod for measuring conductivity or resistivity by supplying an alternating current into a mixed material and measuring the resulting voltage using a group of one resistance and four electrodes.

The conductivity of water increases with increase in the amount of pollutants dissolved in the water. Therefore, the conductivity can be used as an indication of water pollution. In response to the growing interest in environmental protection, the measurement of conductivity is widely performed to detect the degree of water pollution. The conductivity of a material reflects the concentration of impurities contained in the material. Therefore, the measurement of conductivity can be expected to be applied not only to the field of detection of water pollution but also to the field of composition measurement.

The conductivity of soil increases with increase in the amount of water or salt water contained in the soil. The measurement of the conductivity of soil can be expected to be applied to various fields. Examples of applicable fields are detection of the amount of water for irrigation in irrigation cultivation; detection of a situation in which soil containing water weakens, which may lead to a landslide or other similar disaster; detection of the entry of salt water into cultivated land in a coastal region; and detection of the accumulation of salts in soil due to over-watering in a dry region.

There are two methods for measuring conductivity or resistivity, which is the reciprocal of conductivity, i.e. a method in which an electric current and a voltage are measured simultaneously by using only two electrodes, and a method using a group of four electrode to measure an electric current and a voltage independently of each other with respective pairs of electrodes. With the method using only two electrodes, measured data is influenced by a contact potential difference between the electrodes and the material under measurement. In contrast, the method using four electrodes to measure an electric current and a voltage independently of each other can eliminate the influence of contact potential difference.

Further, the measuring method using only two electrodes provides measured data reflecting only a value of conductivity or resistivity of the material under measurement present between the two electrodes, which contains the contact potential difference as an error. However, the measuring method using a group of four electrodes as one electrode system is advantageous in that when the material under measurement extends over a wide area as in the case of the ground, measured data can be made to reflect values of conductivity or resistivity over a wide area by appropriately positioning the electrodes. Further, if a large number of sensors are installed according to the extent of the ground, it is possible to measure the distribution of conductivity or resistivity over a wide area and to observe how the conductivity or resistivity changes with time.

According to the conventional method of measuring conductivity to detect the degree of water pollution, water as a material under measurement is interposed between two electrodes, and the conductivity is obtained as the reciprocal of resistivity between the electrodes. Accordingly, polarization due to electrochemical action occurs at the area of contact between each measuring electrode and water, which makes it impossible to obtain a correct value. Further, to measure a large number of samples, it is necessary to wash the electrodes with fresh water every time the samples are changed.

It is possible to obtain a value of conductivity free from the influence of polarization by using four electrodes in such a manner that two of the four electrodes are used to supply an electric current into a mixed material and the other two electrodes are used to measure an electric potential difference in the mixed material, and obtaining the ratio between the electric current and voltage measured with the respective electrodes (i.e. the measured electric current is divided by the measured voltage). With this method, however, it is not easy to perform division between two analog signals. Therefore, the conventional practice is to use a method wherein a dial is turned by a manual operation, and the dial value when the signal zero point is obtained is read off to obtain a value of conductivity, or a method wherein the measured voltage and electric current are read off as digital signals, and division is executed by a computer.

The resistivity of a material under measurement varies with the temperature of the material regardless of whether the number of electrodes used is two or four. Therefore, even when the composition of impurities in the material under measurement is constant, the conductivity, which is the reciprocal of the resistivity, varies undesirably.

Further, when a plurality of impurities are present in a material under measurement, the content of each impurity element contributes to the overall conductivity. Accordingly, it is impossible to exclusively measure the content of a specific ingredient of interest or changes in the ingredient content.

Thus, an accurate value cannot be obtained with the method using only two electrodes, although this method allows measurement to be carried out easily at site. On the other hand, the method using four electrodes requires much labor at site. Further, both the methods have the disadvantage that measured data is influenced by the temperature of the material under measurement and also by the contribution to the overall conductivity made by ingredients other than a specific ingredient of interest.

In resistivity measurement for the exploration of ground, a plurality of electrodes are horizontally placed in the ground surface to measure resistivity. Resistivity measurement is also performed for the following purposes: detection of the amount of water for irrigation in irrigation cultivation; detection of a situation in which soil containing water weakens, which may lead to a landslide or other similar disaster; detection of the entry of salt water into cultivated land in a coastal region; and detection of the accumulation of salts in soil due to over-watering in a dry region. For these purposes, an electrode system needs to be installed in the ground so as to extend in the direction of depth in order to measure the distribution and time variation of water content or salinity concentration in the direction of depth of the ground.

Accordingly, a large number of electrodes are buried in the ground in a state where they are mounted on a rod-shaped member to perform measurement at a large number of points in the direction of depth. In this case, there is a problem of how to deal with a large number of cables connected to the electrodes. That is, if the cables are routed along the outer wall of the electrode rod, the contact between the cylindrical electrodes and the surrounding soil is degraded. At the same time, the presence of a large number of cables in the soil undesirably influences the distribution and time variation of water content or salinity concentration in the material under measurement. Further, in outdoor measurement, the conductivity or resistivity of the material under measurement changes to a considerable extent with diurnal variations in the underground temperature and hence does not accurately follow the water content or the salinity concentration.

SUMMARY OF THE INVENTION

An object of the present invention is to simplify the operation to be performed at site and to allow temperature variations of a material under measurement to be reflected in the measurement of a current signal, thereby making it possible to perform conductivity measurement free from the influence of temperature variations.

Another object of the present invention is to improve the accuracy of measurement of the amount of a specific substance mixed in a material under measurement.

Still another object of the present invention is to make it possible to readily measure the distribution and time variation of conductivity or resistivity in the direction of depth of soil, a lake, a marsh, etc.

To attain the above-described objects, the present invention provides a system for measuring the amount of a specific substance mixed in a material under measurement. The system includes at least four electrodes placed in the material under measurement in a desired manner. A resistance for measuring an electric current is placed in the material under measurement together with the electrodes. A power supply supplies an alternating current between two of the at least four electrodes through the resistance. A current measuring unit measures an electric current flowing through the resistance. A voltage measuring unit measures an electric potential difference between electrodes of the at least four electrodes other than the electrodes supplied with the alternating current from the power supply. A computing unit obtains a conductivity on the basis of the electric current measured with the current measuring unit, the electric potential difference measured with the voltage measuring unit, and a coefficient determined by the manner in which the at least four electrodes are placed, and subjects the conductivity to conversion based on calibration data to obtain the amount of the specific substance of interest mixed in the material under measurement. The at least four electrodes and the resistance may be supported together as one unit on a support and placed in the material under measurement in a desired manner. The support is at least one plate- or rod-shaped member.

In addition, the present invention provides an electrode rod for measuring conductivity or resistivity by supplying an alternating current into a mixed material and measuring the resulting voltage using a group of one resistance and four electrodes. The electrode rod includes a distal end member formed from a cylindrical member, one end of which is formed into a conical shape. The cylindrical member is integrally formed at the other end thereof with an inner cylindrical portion having an outer diameter smaller than the outer diameter of the cylindrical member by an amount corresponding to the wall thickness of the cylindrical member. The electrode rod further includes a plurality of annular electrodes each having an inner diameter corresponding to the outer diameter of the inner cylindrical portion and a plurality of spacers each having an inner diameter corresponding to the outer diameter of the inner cylindrical portion. A cable lead-in opening is provided in the wall surface of the inner cylindrical portion. The plurality of annular electrodes are fitted onto the outer periphery of the inner cylindrical portion one after another at spacings determined by the spacers, and cables are led to the annular electrodes through the cable lead-in opening. The electrode rod may further include a coupling cylindrical member having the same outer diameter as the outer diameter of the inner cylindrical portion. The coupling cylindrical member is integrally formed at one end thereof with a coupling portion having an inner diameter corresponding to the outer diameter. The inner cylindrical portion may be coupled with the coupling cylindrical member to form a multi-stage structure. The plurality of spacers may include a spacer having a mounting portion for mounting a resistance for detecting an electric current on the wall surface thereof.

In addition, the present invention provides an electrode rod for measuring conductivity or resistivity by supplying an alternating current into a mixed material and measuring the resulting voltage using a group of one resistance and four electrodes. The electrode rod includes a cylindrical member with a conical distal end. Four annular electrodes are fixed on the outer periphery of the cylindrical member at predetermined spacings. A resistance for detecting an electric current is fixed between the annular electrodes. Preferably, the space between second and third annular electrodes of the four annular electrodes is enlarged, and the resistance is fixed between the second and third annular electrodes.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF PREFERRED EMBODIMENTS

Figure 1:
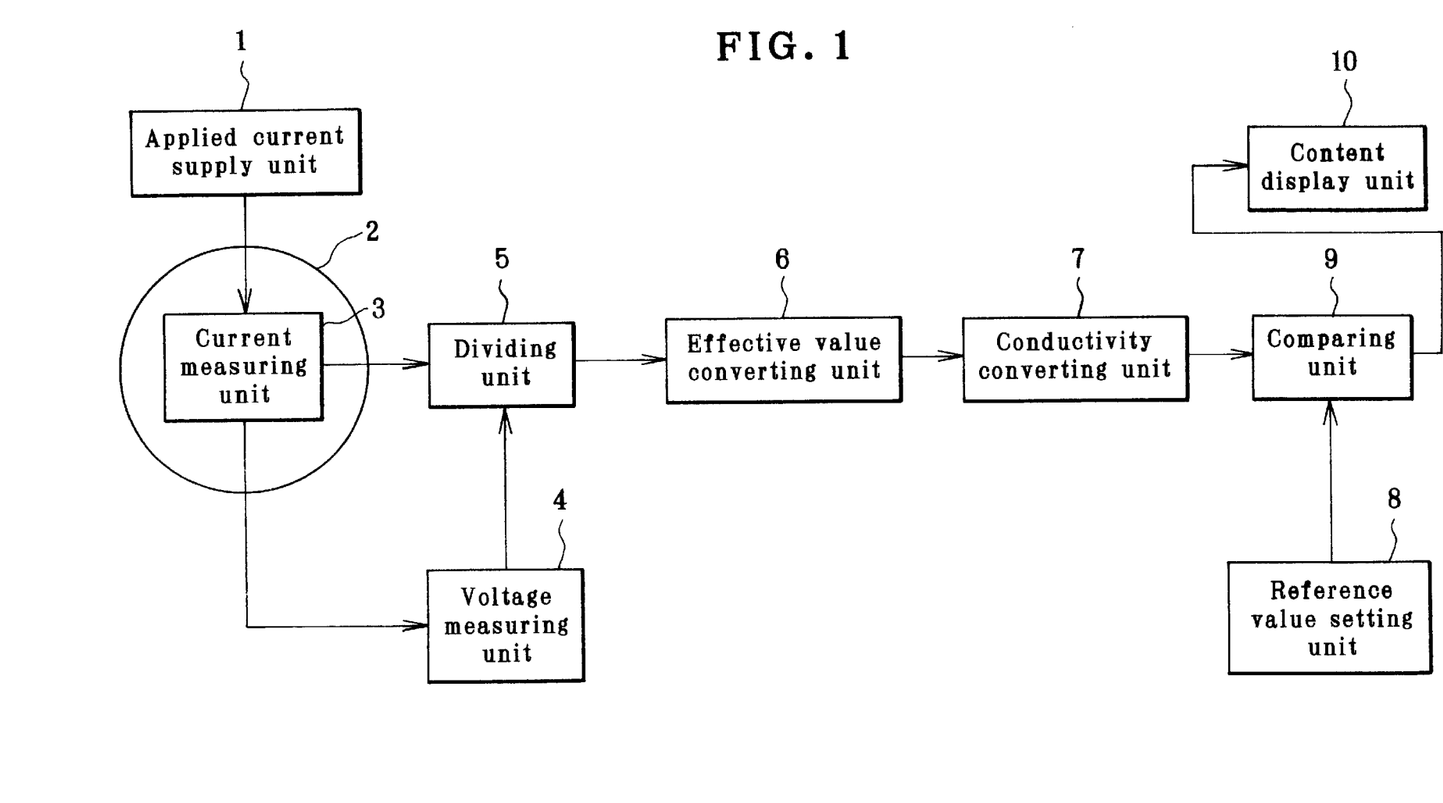
FIG. 1 is a block diagram showing an embodiment of the system for measuring the amount of a specific substance mixed in a material under measurement according to the present invention.

In FIG. 1, an applied current supply unit 1 is a power supply for supplying an alternating current having any desired waveform in which the temporal average value is zero, e.g. a square wave or a sine wave. A material 2 under measurement is any of ground, soil, particulate deposits and fluids which are under various environmental conditions and in which various substances are mixed. Examples of the material 2 under measurement are soil containing water, dune ground and cultivated land near the seaside that are invaded by salt water, land under irrigation cultivation, soil under hothouse cultivation, lakes, marshes and swampy places into which surface water and pollutants are flowing, polluted water in a drainage canal, the mass of landslide, and a slope on the hillside where there is a danger of landslide or other similar disaster. At least four electrodes and a resistance for measuring the applied current are placed in the material 2 under measurement. The electrodes and the resistance are supported together as one unit on a plate- or rod-shaped support. A current measuring unit 3 measures an electric current flowing through the material 2 under measurement when an alternating current is supplied from the applied current supply unit 1 to two of the plurality of electrodes placed in the material 2. More specifically, the current measuring unit 3 is a circuit for measuring an electric current flowing through the resistance placed in the material 2 under measurement, together with the electrodes. A voltage measuring unit 4 is a circuit for measuring a voltage between two of the plurality of electrodes placed in the material 2 under measurement, exclusive of the electrodes supplied with the alternating current. A dividing unit 5 is a circuit for dividing the measured current signal by the measured voltage signal. An effective value converting unit 6 is a circuit for converting the result obtained in the dividing unit 5 into an effective value. A conductivity converting unit 7 is a circuit for converting the effective value into the corresponding value of conductivity. A reference value setting unit 8 is a circuit for setting a value used as a reference for the measurement of conductivity. A comparing unit 9 is a circuit for obtaining a deviation of the measured conductivity from the reference value. A content display unit 10 is a circuit for displaying the measured conductivity in terms of the amount of a specific substance mixed in the material 2 under measurement.

The following is a description of the principle of the method of determining the amount of a specific substance mixed in the material 2 under measurement by measuring conductivity. First, the applied current supply unit 1 generates an alternating current which alternately changes in electrode polarity and whose average value is zero. The applied current supply unit 1 supplies the alternating current into the material 2 under measurement from two of the plurality of electrodes placed in the material 2, causing an electric field to be formed in the material 2. Consequently, an electric potential difference is produced between two other electrodes placed in the material 2. Then, an alternating current flowing through the resistance placed in the material 2 is measured with the current measuring unit 3, and the electric potential difference is measured with the voltage measuring unit 4. Thus, a current signal and a voltage signal are measured independently of each other.

The dividing unit 5 divides the current signal by the voltage signal to obtain a ratio. The ratio thus obtained is proportional to the conductivity of the material 2 under measurement. However, the ratio includes a periodically fluctuating component attributable to the electrical characteristics of the material 2 under measurement. Therefore, the ratio is converted into a DC component equivalent thereto in the effective value converting unit 6. The DC component is proportional to the conductivity of the material 2 under measurement. Then, the DC component is converted into the actual conductivity value in the conductivity converting unit 7. The conductivity thus obtained is the overall conductivity of the material 2 under measurement. Therefore, the reference value setting unit 8 sets a reference value corresponding to the contribution to the overall conductivity made by ingredients other than a specific ingredient of interest. Then, the comparing unit 9 obtains a difference between the overall conductivity of the material 2 under measurement obtained in the conductivity converting unit 7 and the conductivity offered by the ingredients other than the ingredient of interest. The difference is the contribution to the overall conductivity made by only the ingredient of interest. The content display unit 10 displays the difference value as the content of the ingredient of interest according to a calibration curve obtained in advance.

Elimination of Temperature Characteristics of the Material Under Measurement In a case where the material under measurement spreads outdoors as in the measurement of the salinity concentration or water content in soil or the degree of pollution of lake water, the conductivity of the material under measurement is influenced by diurnal variations in the outside air temperature and so forth. In such a case, conductivity is expressed as follows:

$$\sigma = \frac{1}{\rho} = \frac{1}{\rho_0(1+\alpha\theta)} \qquad (1)$$

In Eq. (1): $\sigma$ is the conductivity of the material under measurement; $\rho$ is the resistivity of the material under measurement; $\theta$ is the temperature of the material under measurement; $\alpha$ is the temperature coefficient of resistance of the material under measurement; and $\rho_0$ is the resistivity when $\theta=0$. Accordingly, the voltage measured in the voltage measuring unit 4 is expressed as follows:

$$v_p = k_p \rho_0 (1+\alpha\theta) i \qquad (2)$$

In Eq. (2): $v_p$ is the measured voltage; $k_p$ is a coefficient determined by the placement and configuration of the electrode system; and i is the applied current. In the current measuring unit 3, a resistance for measuring the applied current is inserted in the current circuit, and the voltage across the resistance is expressed as the magnitude of electric current. Therefore, the magnitude of electric current is expressed as follows:

$$v_c = Ri \qquad (3)$$

In Eq. (3): $v_c$ is the voltage across the resistance for measuring the applied current; R is the resistance value of the applied current measuring resistance; and i is the applied current. Thus, $v_c$ is proportional to the magnitude of the applied current i.

The output from the dividing unit 5 is the result of dividing the value of Eq. (3) by the value of Eq. (2). Because the value of the quotient is proportional to the conductivity, the conductivity to be obtained is expressed as follows:

$$\sigma = k_\sigma \frac{v_c}{v_p} = k_\sigma \frac{Ri}{k_p \rho_0 (1+\alpha\theta) i} = k \frac{R}{\rho_0 (1+\alpha\theta)} \quad (4)$$

In Eq. (4): $k_\sigma$ is a proportional constant; and k is a constant such that $k=k_\sigma/k_p$. Eq. (4) contains a term varying with temperature of the material under measurement, i.e. $(1+\alpha\theta)$. Regarding Eq. (3), if the resistance R for measuring the applied current is placed in the material under measurement, R is under the influence of temperature variations similar to those which influence the material under measurement. Therefore, in Eq. (3), R is replaced as follows:

$$R \rightarrow R_0(1+\beta\theta) \quad (5)$$

In Eq. (5), $(1+\beta\theta)$ is a term varying with temperature of $R_0$. $R_0$ is the resistivity of the resistance, the voltage across which is proportional to the applied current, when $\theta=0$. When $\alpha=\beta$, Eq. (4) is expressed as follows:

$$\sigma = k_\sigma \frac{v_c}{v_p} = k_\sigma \frac{R_0(1+\beta\theta)i}{k_p \rho_0 (1+\alpha\theta) i} = k \frac{R_0}{\rho_0} \quad (6)$$

According to Eq. (6), the output from the dividing unit 5 does not contain a term varying with temperature of the material under measurement. Thus, the dividing unit 5 outputs a value proportional to the conductivity of the material under measurement. With the present invention, because a resistance for measuring the applied current is placed in the material under measurement, the conductivity of the material under measurement alone can be measured as shown in Eq. (6). In this case, the temperature characteristics of the resistance need not precisely agree with the temperature characteristics of the material under measurement. However, the influence of temperature variations decreases according as the temperature characteristics of the resistance become closer to the temperature characteristics of the material under measurement.

Extraction of Data Concerning the Ingredient of Interest from the Material Under Measurement In the actual measurement, the material under measurement contains not only the ingredient (impurity) of interest but also other ingredients. In such a case, the conductivity of the material under measurement is expressed as follows:

$$\sigma = \sigma_0 + \sigma_a \quad (7)$$

In Eq. (7): $\sigma$ is the overall conductivity of the mixture; $\sigma_0$ is the conductivity offered by the ingredients (impurities) other than the ingredient of interest; and $\sigma_a$ is the conductivity offered by the ingredient of interest alone. The output from the conductivity converting unit 7 shown in FIG. 1 is the overall conductivity given by the Eq. (7). Accordingly, the conductivity of the ingredient of interest can be obtained by subtracting the conductivity $\sigma_0$ of the ingredients other than the ingredient of interest, which is set in the reference value setting unit 8, from the output of the conductivity converting unit 7. The output from the comparing unit 9 is the conductivity of only the ingredient of interest. Therefore, the conductivity can be displayed in terms of the content of the ingredient of interest through conversion using a calibration curve obtained separately.

Figure 2:
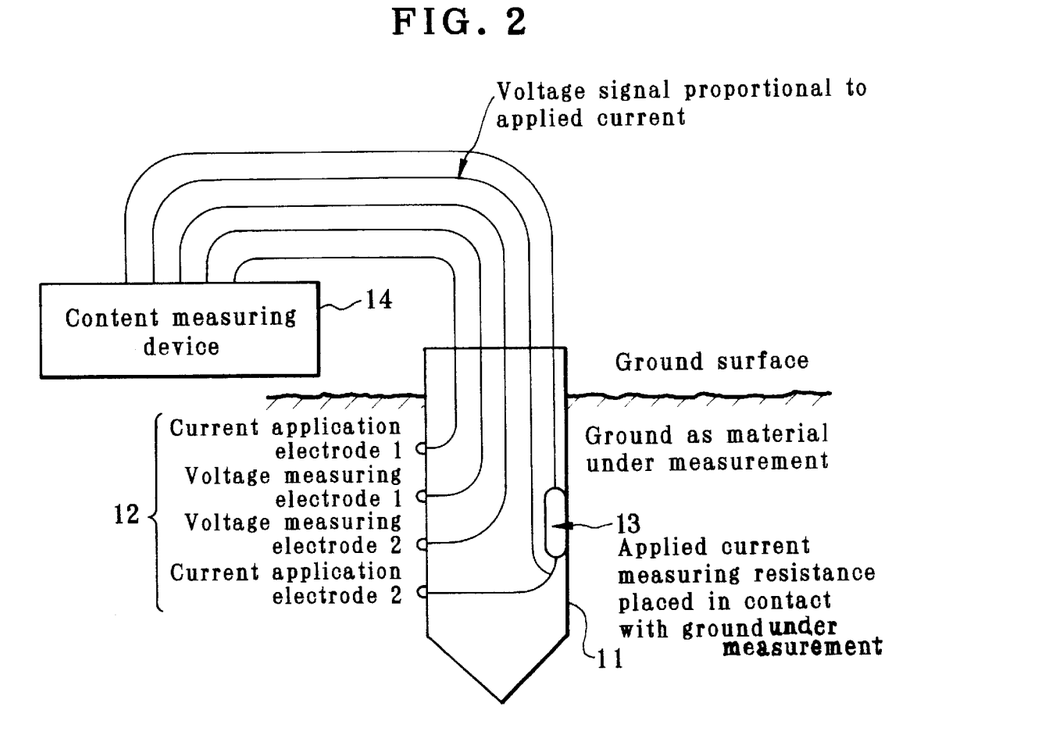
FIG. 2 is a diagram showing an example of placement of electrodes and an applied current measuring resistance in a case where the water content in the ground is to be measured.

In the foregoing system for measuring the amount of a specific substance mixed in a material under measurement according to the present invention, as shown in FIG. 2 by way of example, an electrode support member 11 is disposed to extend into the ground as a material under measurement from the ground surface. The electrode support member 11 supports electrodes 12 and a resistance 13 for measuring the applied current together as one unit. In this state, an alternating current is supplied between two of the electrodes 12. The applied current is measured with the resistance 13, and an electric potential difference between two other electrodes 12 is measured, whereby the water content in the ground is measured.

Figure 3A:
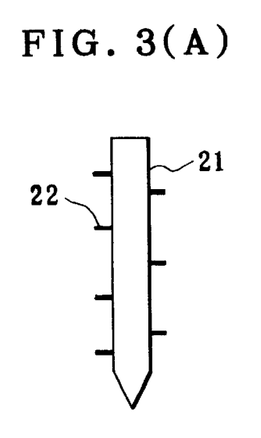
FIG. 3 is a diagram showing structural examples of a member for supporting electrodes.
Figure 3B:
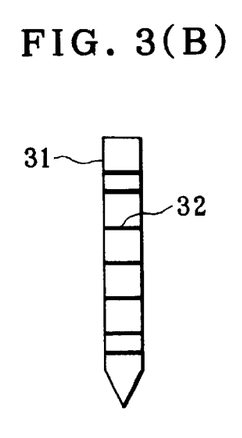
Figure 3C:
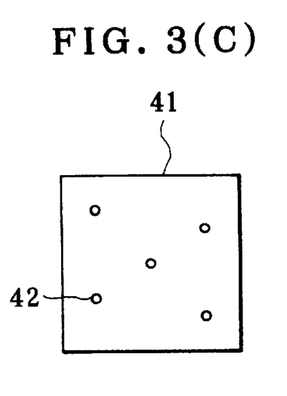
Figure 4:
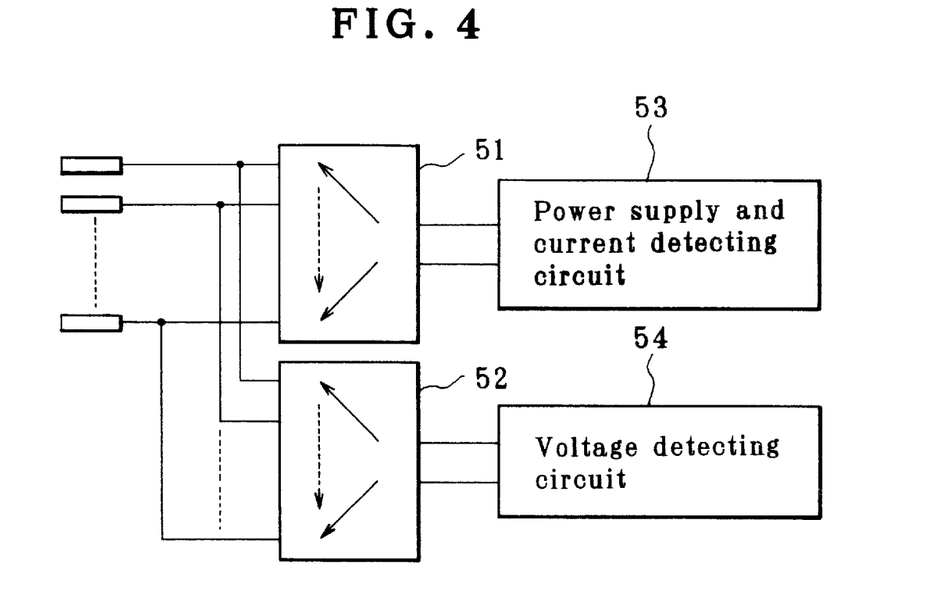
FIG. 4 is a diagram showing a structural example of an electrode switching circuit.

Electrodes used in the system for measuring the amount of a specific substance mixed in a material under measurement according to the present invention includes electrodes for supplying an electric current into the material under measurement and electrodes for measuring an electric potential difference at an area of interest in the material under measurement as stated above. Accordingly, the electrodes may be arranged as follows. As shown in FIG. 3, a plurality of electrodes 22, 32 or 42 are supported on an electrode support member 21, 31 or 41. As shown in FIG. 4 by way of example, the electrodes are connected to a power supply and current detecting circuit 53 for selectively supplying an electric current. Alternatively, electrode switching circuits 51 and 52 are inserted between the electrodes on the one hand and the power supply and current detecting circuit 53 and a voltage detecting circuit 54 on the other so that the electrodes are selectively connected to the voltage detecting circuit 54 to detect an electric potential difference. It is a matter of course that each electrode is assigned to serve as a current electrode or a voltage electrode, and the current electrodes and the voltage electrodes are connected directly to the power supply and current detecting circuit 53 and the voltage detecting circuit 54, respectively, without using the electrode switching circuits 51 and 52. The arrangement may also be such that the power supply and current detecting circuit 53 and the voltage detecting circuit 54 are each provided with ports, the number of which corresponds to the number of electrodes, and the ports are switched over sequentially.

Regarding the arrangement of electrodes and an electrode support member constituting a measuring unit, a plurality of electrodes 22 may be supported on a rod-shaped (stake-shaped) electrode support member 21 as shown in part (A) of FIG. 3. Alternatively, as shown in part (B) of FIG. 3, a plurality of annular electrodes 32 may be supported on a rod-shaped (stake-shaped) electrode support member 31. As shown in part (C) of FIG. 3, a plurality of projecting electrodes 42 may be supported on a plate-shaped electrode support member 41.

When an electric current is supplied into the material under measurement from a pair of electrodes, the voltages at a plurality of areas can be detected with a plurality of pairs of electrodes. In such a case, a voltage detecting circuit is sequentially connected to the plurality of pairs of voltage detecting electrodes through an electrode switching circuit to detect voltages. The detected voltage values are subjected to analog-to-digital conversion, together with the current value, and stored in a memory. Thereafter, the amount of the specific substance mixed in the material under measurement is obtained for each area. The content of the specific substance may be obtained in either the on-line or off-line mode. Data concerning the content of the specific substance obtained at each area may be directly displayed as a table and printed out. Alternatively, the data may be stored in a memory before being outputted. It is a matter of course that the data may be displayed for each detection area by performing a switching operation appropriately.

Figure 5:
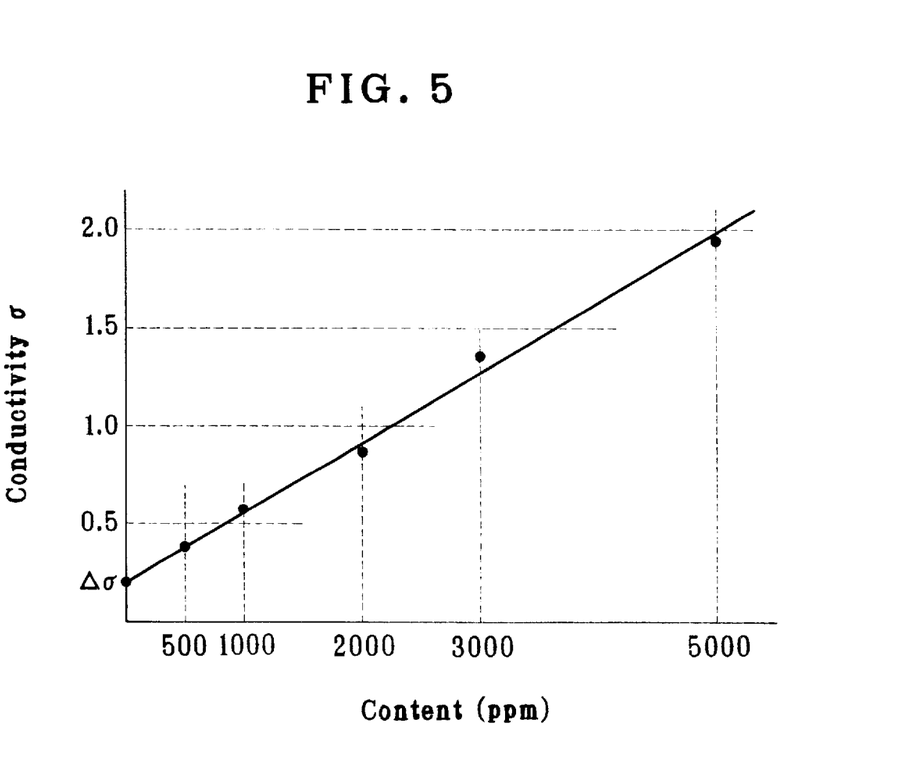
FIG. 5 is a diagram showing the relationship between the salinity concentration in soil saturated with water and the level of the output signal as an example of measurement of the content of a specific ingredient.

Next, an example of measurement of the content of a specific ingredient will be shown. FIG. 5 is a diagram showing the relationship between the salinity concentration in soil saturated with water and the level of the output signal as an example of measurement of the content of a specific ingredient. In this example, conductivity a was measured for each of samples having a salinity concentration of 0 ppm, 500 ppm, 1000 ppm, 2000 ppm, 3000 ppm and 5000 ppm, respectively. It will be clearly understood from FIG. 5 that the salinity concentration (ppm) in soil saturated with water is in proportional relation to the conductivity σ. Accordingly, the salinity concentration (ppm) can be obtained from the conductivity σ by computation. If a table for conversion of the conductivity σ to the salinity concentration (ppm) is set by using a look-up table, for example, the salinity concentration (ppm) can be obtained directly from the conductivity σ by referring to the conversion table. It is also possible to set a conversion table for obtaining the content of a specific substance from the current value and the voltage value.

Figure 6:
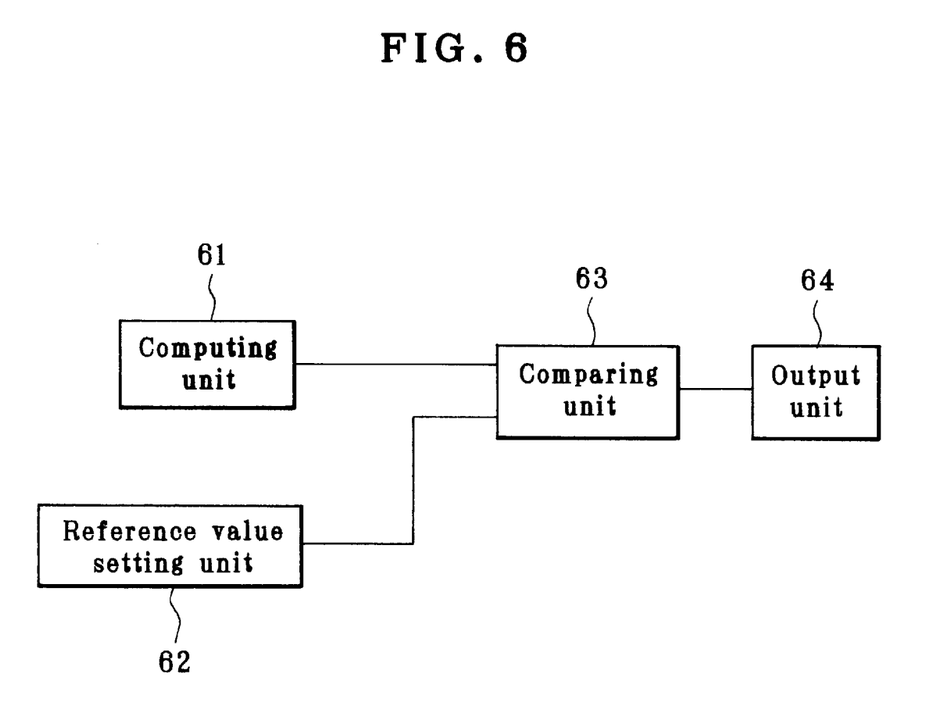
FIG. 6 is a block diagram showing an embodiment of the system for monitoring the content of a specific ingredient in a mixed material according to the present invention.

In FIG. 6, a computing unit 61 obtains the content of a specific ingredient by performing computation and referring to a conversion table on the basis of a current value, a voltage value, a coefficient depending on the electrodes used, and the contribution to detection data made by ingredients other than the specific ingredient, as has been stated above. A reference value setting unit 62 sets at least one reference value for evaluation of the content of the specific ingredient. A comparing unit 63 compares the content of the specific ingredient obtained in the computing unit 61 with the reference value set in the reference value setting unit 62. An output unit 64 outputs information indicating whether or not the content of the specific ingredient obtained in the computing unit 61 exceeds the reference value set in the reference value setting unit 62. If a plurality of reference values have been set, comparison information can be outputted stepwisely as the content of the specific ingredient increases. For example, in monitoring the amount of water contained in soil, it is possible to give a precautionary warning or other warning.

It should be noted that the present invention is not limited to the foregoing embodiments but can be modified in a variety of ways. For instance, in the foregoing embodiments a plurality of electrodes and a resistance for measuring the applied current are supported together as one unit on a single support member and placed in a material under measurement in a desired manner. However, a plurality of electrodes and a resistance for measuring the applied current may be dispersedly supported on a plurality of supports. Regarding the support configuration, planar supports, that is, plate-shaped supports, may also be used in addition to the rod-shaped supports. Although in the foregoing embodiments the electrodes are inserted into the material under measurement so as to be arranged in the direction of depth thereof, it is also possible to bury the electrodes in the bottom of the material under measurement or to place the electrodes on the bottom or wall surface of a storage container. Although the present invention has been described above with regard to the measurement of the content of water or salt mixed in the material under measurement, it is possible to apply the present invention to observation of any material in which an ingredient dominantly changing in amount can be specified. The present invention allows observation of changes in the amount of the specific ingredient exclusively. That is, the present invention is applicable to the observation of the accumulation of salts in semi-dry ground and also applicable to the observation of soil pollution with chemical substances. Similarly, the present invention is usable in an apparatus for mixing a specific substance as a device for detecting the amount of the specific substance mixed in the apparatus.

As will be clear from the foregoing description, the present invention enables the conductivity or the amount of a specific ingredient in a mixture to be obtained accurately and instantaneously and hence allows the operating efficiency to be improved when used at site in the open air or the like. Moreover, the influence of temperature variations on the conductivity of the material under measurement can be eliminated directly from the analog signal, which has heretofore been impossible to do. Therefore, it is possible to obtain the accurate conductivity or content of the ingredient of interest. Further, measurement is carried out with a group of four electrodes for each electrode system. In this regard, if each electrode system uses electrodes of the same configuration, the coefficient inherent in the electrode system for conductivity measurement is constant. Therefore, if calibration has previously been performed for one group of electrodes constituting an electrode system, conductivity can be obtained immediately even in multi-point, simultaneous measurement. Accordingly, if the density and composition are the same throughout a material under measurement, e.g. soil, it is possible to obtain the distribution of content of a specific ingredient, e.g. water, at different places in the same way as the above by obtaining a calibration curve in advance.

In a case where a large number of electrode systems are buried in a material under measurement to observe changes in the water content or the like with time in both the direction of depth and the direction of planar extent for a long period of time, it is possible to observe changes in the water content or the like most accurately because the observation is not influenced by temperature variations of the material under measurement and there is no change in the density and composition of the material except for the ingredient of interest. The effects of the present invention are expected to be manifested most remarkably when it is applied to fields in which observation has to be made for a long period of time. Examples of such fields of application are monitoring of the amount of water for irrigation in irrigation cultivation; detection of a situation in which soil containing water weakens, which may lead to a landslide or other similar disaster; observation of the entry of salt water into cultivated land in a coastal region; and detection of the accumulation of salts in soil due to over-watering in a dry region.

In a mixed substance in which a plurality of impurities are mixed, if there is one ingredient of interest that changes in amount with time, a reference value is set so that the output of the measuring device is zero at the time of starting observation, whereby the varying amount of the ingredient of interest can be measured with ease simply by defining the state before the starting of measurement as a reference value. This is very useful for on-site observation in the open air or the like.

Figure 7:
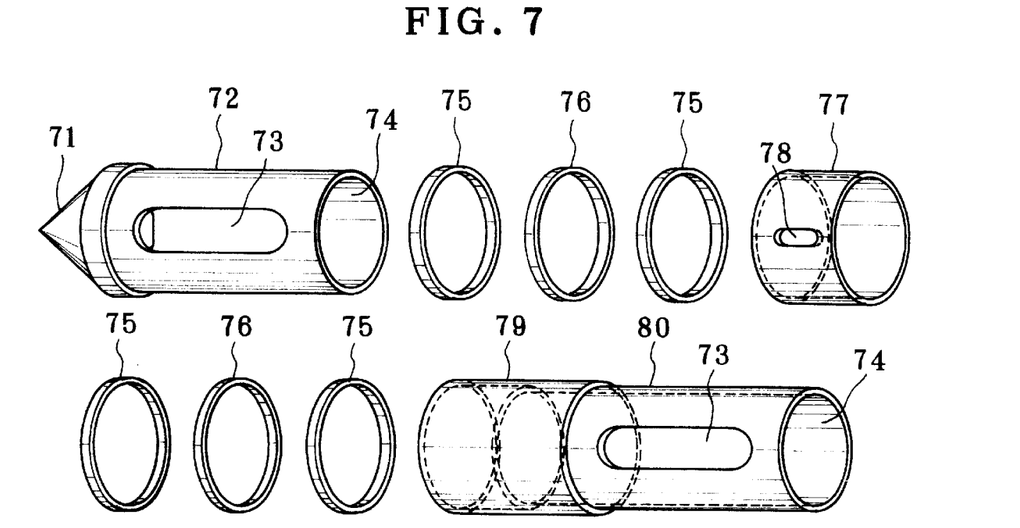
FIG. 7 is a diagram showing an embodiment of the electrode rod for measurement according to the present invention.

The following is a description of an embodiment of an electrode rod for measuring conductivity or resistivity according to the present invention. In FIG. 7, a distal end member 71 forms a forward end portion of the electrode rod when placed in the ground or water so as to extend in the direction of depth. The distal end member 71 is a cylindrical member, one end of which is formed into a conical shape to reduce resistance offered from the ground when the electrode rod is thrust thereinto from the ground surface. An inner cylindrical portion 72 is integrally formed at the other end of the cylindrical member. The inner cylindrical portion 72 has an outer diameter smaller than the outer diameter of the cylindrical member by an amount corresponding to the wall thickness of the cylindrical member. The inner cylindrical portion 72 has a cable lead-in opening 73 in a part of the wall surface thereof. A coupling cylindrical member 79 is integrally formed at one end thereof with a coupling portion having an inner diameter corresponding to the outer diameter of the inner cylindrical portion 72. That is, the coupling cylindrical member 79 is integrally formed with a coupling portion similar to the cylindrical portion of the distal end member 71. The coupling cylindrical member 79 has an inner cylindrical portion 80 with the same outer diameter as that of the inner cylindrical portion 72. The inner cylindrical portion 72 is fitted into the coupling cylindrical member 79 so as to join to the inner cylindrical portion 80 with substantially no gap therebetween. Thus, the coupling cylindrical member 79 allows the inner cylindrical portions 72 and 80 to be coupled together in a plurality of stages. The inner cylindrical portion 80 of the coupling cylindrical member 79 also has a cable lead-in opening 73 similar to that of the inner cylindrical portion 72, which is formed in a part of the wall surface thereof. Annular electrodes 75 and spacers 76 and 77 each have an inner diameter corresponding to the outer diameter of the inner cylindrical portions 72 and 80 so as to be fitted on the outer periphery of each of the inner cylindrical portions 72 and 80 with substantially no gap therebetween. The spacer 76 fixes annular electrodes 75 fitted on each of the inner cylindrical portions 72 and 80 at a short spacing. The spacer 77 fixes annular electrodes 75 fitted on each of the inner cylindrical portions 72 and 80 at a long spacing. The spacer 77 has a mounting portion 78 for mounting a resistance for measuring an electric current.

The following is a description of an electrode rod for measuring conductivity or resistivity assembled by using the above-described members. First, an annular electrode 75, a spacer 76 and an annular electrode 75 are fitted onto the inner cylindrical portion 72 of the distal end member 71 from the hollow portion 74 side in the order mentioned as one set. Next, a spacer 77 is fitted onto the inner cylindrical portion 72. Then, an annular electrode 75, a spacer 76 and an annular electrode 75 are fitted onto the inner cylindrical portion 72 in the order mentioned as one set. Then, the coupling cylindrical member 79 is fitted onto the inner cylindrical portion 72. Thus, the four annular electrodes 75 are fixed on the inner cylindrical portion 72 with the spacers 76, 77 and 76 placed therebetween. At this time, cables from the four annular electrodes 75 and the current measuring resistance mounted on the mounting portion 78 of the spacer 77 are led out by using the cable lead-in opening 73 and the space in the hollow portion 74.

When annular electrodes 75 are to be mounted to form a multi-stage structure, an annular electrode 75, a spacer 76, an annular electrode 75, a spacer 77, an annular electrode 75, a spacer 76, an annular electrode 75 and a coupling cylindrical member 79 are fitted onto the inner cylindrical portion 80 in the order mentioned in the same way as the above. The number of stages can be increased by repeating the above-described procedure.

If a projection is provided on the outer periphery of each annular electrode 75, when the electrode rod is installed in the ground, the annular electrode 75 can keep contact with the surrounding ground in a favorable condition. An electrode constant inherent in the electrode system is determined by electrode spacings, which, in turn, are determined by the annular electrodes 75, the spacers 76 and 77, and the coupling cylindrical member 79. When a group of four electrodes 75 constitutes one electrode system, the coupling cylindrical member 79 determines the spacing between one electrode system and another electrode system adjacent thereto. The length of the coupling cylindrical member 79 can be determined so that the electrode systems are installed at the desired depths in the ground. Accordingly, if a plurality of different kinds of spacers 76 and 77 and coupling cylindrical members 79, which vary in length, are prepared, it is possible to select electrode spacings in conformity to each particular purpose.

Cables from each annular electrode 75 and the current measuring resistance are routed through the hollow portion 74 and led out from the other end of the electrode rod (i.e. the upper end of the electrode rod when installed in the ground). To fabricate an electrode rod for measuring conductivity or resistivity as stated above, it is necessary that every time a portion of the electrode is assembled, an insulating material should be filled in the assembled portion to prevent the circuit from short-circuiting even when the material under measurement is a liquid.

Next, measurement of conductivity with the electrode rod will be described. First, the electrode rod is installed in the ground such that the distal end member 71 faces in the direction of depth of the ground. Consequently, a plurality of electrode systems each comprising a group of four electrodes are fixed at predetermined depths in respective regions of the ground. The cables are led out to the ground surface through the hollow portion of the electrode rod. Therefore, the periphery of the electrode rod in the ground is in contact with the soil uniformly. Accordingly, the presence of the electrode rod has no influence on the phenomenon of changes in conductivity or resistivity in each region of the ground due to rainfall infiltration or the entry of salt water. In addition, each annular electrode has a small projection on the surface thereof, which allows the annular electrode to keep contact with the surrounding soil. Moreover, because each electrode system has the same configuration and electrode spacings, the electrode constant thereof is the same. Accordingly, the conductivity distribution in the direction of depth of the ground can be observed by measuring conductivity or resistivity while sequentially switching the plurality of electrode systems attached to the electrode rod.

Figure 8:
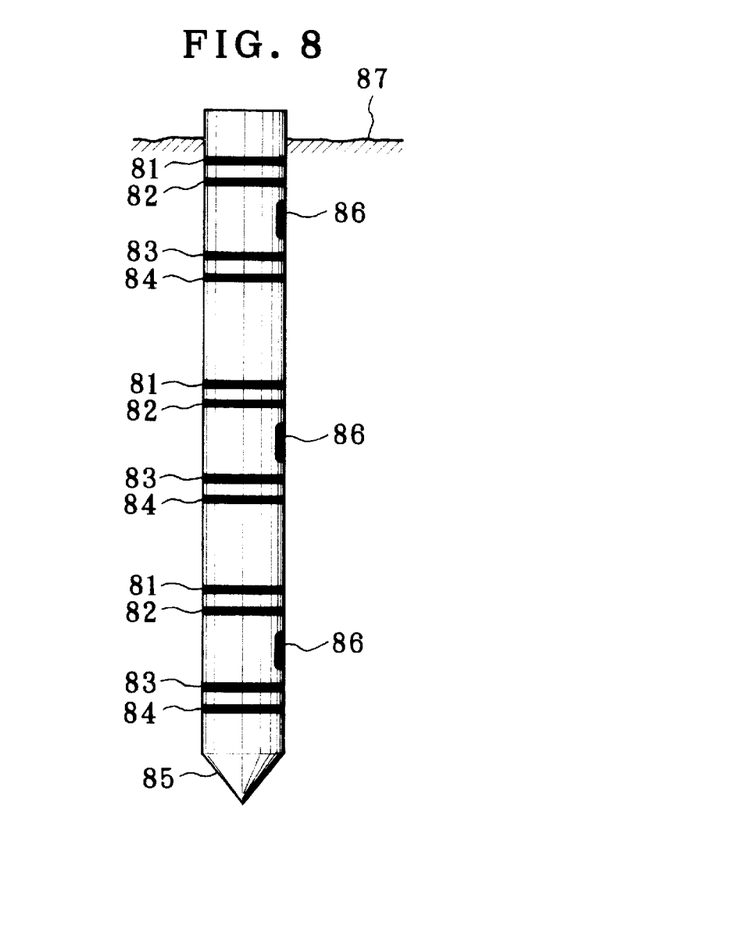
FIG. 8 is a diagram showing an example in which an electrode rod with three electrode systems each consisting of a group of four electrodes is buried in the ground.

In a case where conductivity or resistivity is measured by using, as shown in FIG. 8, groups of four annular electrodes 81 to 84 mounted on an electrode rod thrust into the ground from the ground surface 87, an electric current is applied to the ground from the annular electrodes 81 and 84 to form an electric current field in the ground. The electric potential difference between the annular electrodes 82 and 83 is measured, and the ratio of the applied current to the electric potential difference is obtained as conductivity. Alternatively, resistivity is obtained as the reciprocal of the conductivity. It should be noted that the annular electrodes 81 to 84 correspond to the annular electrodes 75 in FIG. 7. The spacing between the annular electrodes 81 and 82 and the spacing between the annular electrodes 83 and 84 correspond to the spacers 76, respectively, in FIG. 7. The spacing between the annular electrodes 82 and 83 corresponds to the spacer 77 in FIG. 7. The spacing between the annular electrodes 81 and 84 corresponds to the coupling cylindrical member 79 in FIG. 7. The distal end 85 corresponds to the distal end member 71 in FIG. 7.

In a case where the material under measurement spreads outdoors as in the measurement of the salinity concentration or water content in soil or the degree of pollution of lake water, the conductivity of the material under measurement is influenced by diurnal variations in the outside air temperature and so forth. In such a case, conductivity is expressed as represented by the foregoing Equation (1). The electric potential difference between the annular electrodes 82 and 83 is expressed as represented by the foregoing Equation (2).

To measure the electric current applied from the annular electrodes 81 and 84, a resistance 86 for measuring electric current is inserted in series to the circuit of the annular electrodes 81 and 84. Consequently, the voltage across the resistance 86 is proportional to the applied current. Because each current measuring resistance 86 is mounted on the surface of the electrode rod in contact with the material under measurement, the resistance 86 is under the same influence of temperature variations as that exerted upon the material under measurement. The magnitude of the applied current is expressed as follows:

$$v_c = R_0(1+\beta\theta)i \tag{8}$$

In Eq. (8): $v_c$ is the electric potential difference across the current measuring resistance; $R_0$ is the resistance value when $\theta=0$; and $\beta$ is the temperature coefficient of resistance of R. In the present invention, the current measuring resistance 86 is installed on the surface of the electrode rod and in the center of each of the four electrode systems so as to be in contact with the material under measurement. Therefore, $\theta$ in Eq. (8) may be regarded as the same as $\theta$ in Eq. (2), which is the temperature of the material under measurement. Accordingly, the conductivity of the material under measurement is proportional to the ratio of Eq. (8) to Eq. (2). Hence, when $\alpha=\beta$, the conductivity $\sigma$ is expressed as follows:

$$\sigma = k_\sigma \frac{v_c}{v_p} = k_\sigma \frac{R_0(1+\beta\theta)i}{k_p \rho_0(1+\alpha\theta)i} = k\frac{R_0}{\rho_0} \tag{9}$$

In Eq. (9): $k_o$ is a proportional constant; and k is a constant such that $k=k_o/k_p$. The conductivity $\sigma$ obtained from Eq. (9) does not contain a term varying with temperature of the material under measurement. Thus, the value obtained is proportional to only the conductivity of the material under measurement. In this case, the temperature characteristics of the resistance need not completely agree with the temperature characteristics of the material under measurement. However, the influence of temperature variations decreases according as the temperature characteristics of the resistance become closer to the temperature characteristics of the material under measurement.

Figure 9:
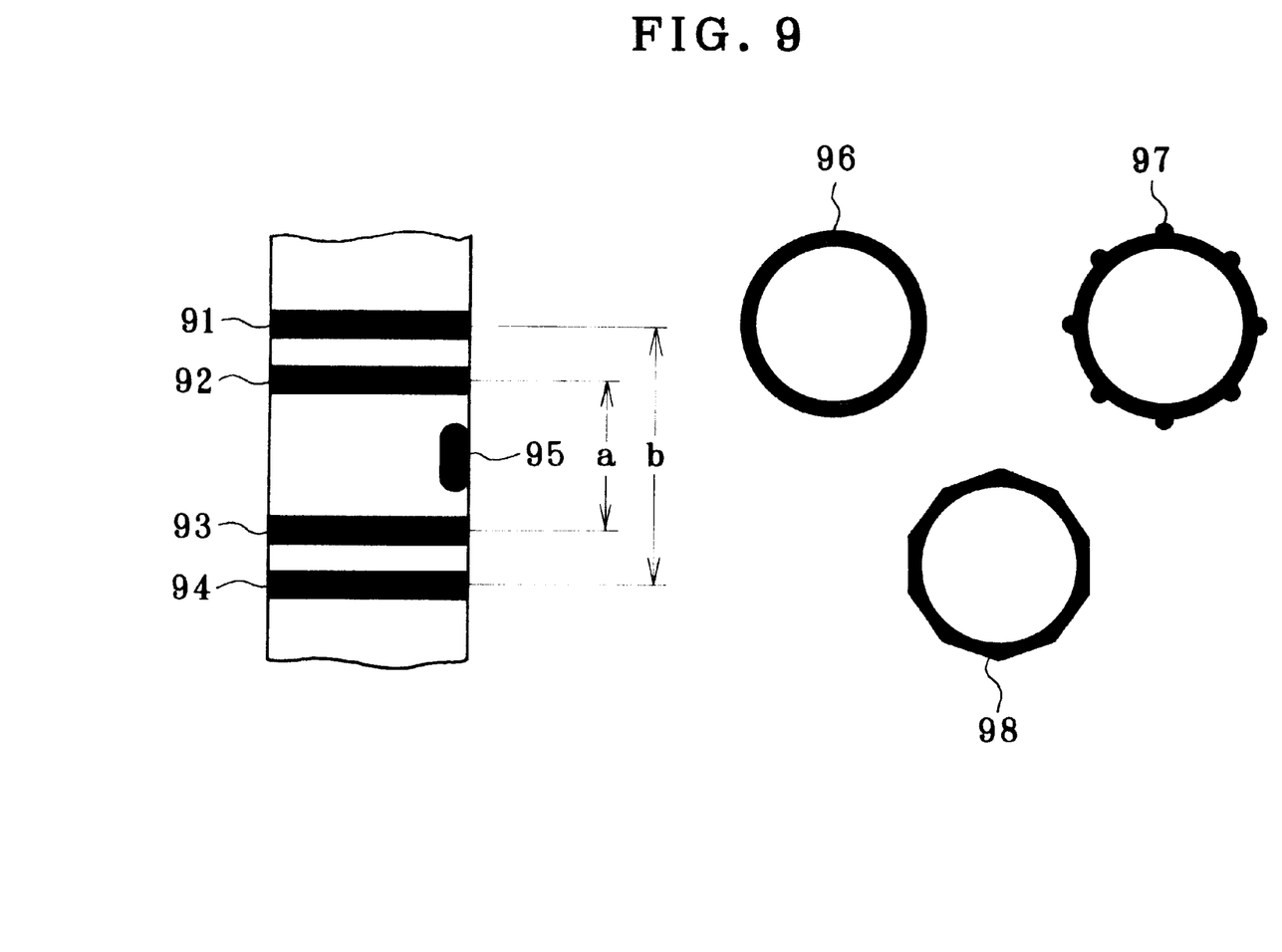
FIG. 9 is a diagram showing another embodiment of the electrode rod for measurement according to the present invention, which has four annular electrodes with various configurations.

In an electrode system comprising four electrodes, the measured conductivity or resistivity is allowed to reflect influences over a wide area of the material under measurement if, as shown in FIG. 9, the spacing a between electric potential difference measuring electrodes 92 and 93 is widened and the spacing b between current application electrodes 91 and 94 is also widened. On the other hand, if the spacings a and b are narrowed, local measurement can be carried out. Accordingly, to measure a planar distribution over an extensive area of the outdoor ground, the electrode spacings a and b are set wide, whereby representative values can be measured. When it is desired that measured values should reflect changes in the water content in the direction of depth or the like, the electrode spacings a and b are set narrow, and a large number of electrode systems each comprising a group of four electrodes with the spacings a and b are installed. By doing so, the water content distribution in the direction of depth can be observed finely.

When the electrode rod has a large diameter and each annular electrode has a large width in the direction of the center line, the annular electrodes can keep contact with the surrounding material under measurement in a favorable condition. Therefore, the annular electrodes may have a configuration such as that of an annular electrode 96. However, when it is desired to measure changes in conductivity at reduced sensor spacings, it is necessary to reduce the size of the electrode rod and the size of the annular electrodes as well as the electrode spacings. Therefore, the condition of contact with the material under measurement may be degraded according to the installation conditions. In such a case, the annular electrodes should preferably be provided with projections such as those of annular electrodes 97 and 98. By doing so, a favorable contact condition can be maintained. Variations in the measured values due to the difference in electrode configuration can be calibrated with the coefficient k in Eq. (9).

As will be clear from the foregoing description, the electrode rod according to the present invention has a round bar-like external shape and is therefore easy to install in outdoor ground. In a group of four electrodes constituting an electrode system, a pair of electrodes are used as current application electrodes, and the other pair of electrodes as voltage measuring electrodes. Therefore, it is possible to perform measurement independent of the contact resistance between the voltage measuring electrodes and the material under measurement. Accordingly, once it has been installed, the electrode rod needs no inspection and so forth thereafter. Thus, maintenance costs can be reduced. Moreover, there is no particular restriction on the electrode material. Accordingly, an inexpensive and durable material such as brass can be used as a material for electrodes. For spacers, it is also possible to use an inexpensive and durable material such as polyvinyl chloride pipe. Accordingly, a robust electrode rod can be constructed.

Further, because an electric current measuring resistance is incorporated into the electrode rod, it is possible to eliminate or reduce the influence of temperature variations on the measurement of conductivity of the material under measurement. In particular, in a case where a large number of electrode systems are buried in a material under measurement to observe, for example, changes in the water content in the ground with time in both the direction of depth and the direction of planar extent for a long period of time, it is possible to observe changes in the water content accurately because the influence of temperature variations of the material under measurement is reduced and there is no change in the density and composition of the material except for the ingredient of interest.

The effects of the present invention are expected to be manifested most remarkably when it is applied to fields in which observation has to be made for a long period of time, i.e. monitoring of the amount of water for irrigation in irrigation cultivation; detection of a situation in which soil containing water weakens, which may lead to a landslide or other similar disaster; observation of the entry of salt water into cultivated land in a coastal region; and detection of the accumulation of salts in soil due to over-watering in a dry region.

Furthermore, a desired number of points of measurement can be provided by installing electrode systems each comprising a group of four electrodes at desired spacings. If a large number of electrode rods each having a plurality of electrode systems in the direction of depth are placed in a planar field, it is possible to carry out measurement while switching over the sensors from one to another. Accordingly, it is possible to perform three-dimensional measurement in the ground over a wide area. Moreover, it is possible according to the present invention to perform measurement while switching over the points of measurement in the direction of depth. Therefore, the present invention requires only one measuring device to perform the measurement. In a method wherein a large number of points of measurement are scanned, because measurement of analog signals is performed with a single device, there are no variations in errors which might otherwise be introduced by different measuring devices into measured values at different points of measurement.

I claim:

1. A system for measuring an amount of a specific substance mixed in a material under measurement, said system comprising:
    at least four electrodes placed in the material under measurement in a desired manner;
    a resistance for measuring an electric current placed in said material under measurement together with said electrodes;
    a power supply for supplying an alternating current between two of said at least four electrodes through said resistance;
    current measuring means for measuring an electric current flowing through said resistance;
    voltage measuring means for measuring an electric potential difference between electrodes of said at least four electrodes other than the electrodes supplied with the alternating current from said power supply; and
    computing means for obtaining a conductivity on a basis of the electric current measured with said current measuring means, the electric potential difference measured with said voltage measuring means, and a coefficient determined by a manner in which said at least four electrodes are placed, and for subjecting said conductivity to conversion based on calibration data to obtain an amount of said specific substance of interest mixed in said material under measurement.

2. The system of claim 1, wherein said at least four electrodes and said resistance are supported together as one unit on a support and placed in the material under measurement in a desired manner.

3. The system of claim 2, wherein said support comprises at least one plate- or rod-shaped member.

4. An electrode rod for measuring conductivity or resistivity by supplying an alternating current into a mixed material and measuring a resulting voltage using a group of one resistance and four electrodes, said electrode rod comprising:
    a distal end member formed from a cylindrical member, one end of which is formed into a conical shape, said cylindrical member being integrally formed at the other end thereof with an inner cylindrical portion having an outer diameter smaller than an outer diameter of said cylindrical member by an amount corresponding to a wall thickness of said cylindrical member;
    a plurality of annular electrodes each having an inner diameter corresponding to the outer diameter of said inner cylindrical portion;
    a plurality of spacers each having an inner diameter corresponding to the outer diameter of said inner cylindrical portion; and
    a cable lead-in opening provided in a wall surface of said inner cylindrical portion;
    wherein said plurality of annular electrodes are fitted onto an outer periphery of said inner cylindrical portion one after another at spacings determined by said spacers, and cables are led to said annular electrodes through said cable lead-in opening.

5. An electrode rod for measuring conductivity or resistivity by supplying an alternating current into a mixed material and measuring a resulting voltage using a group of one resistance and four electrodes, said electrode rod comprising:
    a distal end member formed from a cylindrical member, one end of which is formed into a conical shape, said cylindrical member being integrally formed at the other end thereof with an inner cylindrical portion having an outer diameter smaller than an outer diameter of said cylindrical member by an amount corresponding to a wall thickness of said cylindrical member;
    a plurality of annular electrodes each having an inner diameter corresponding to the outer diameter of said inner cylindrical portion;
    a plurality of spacers each having an inner diameter corresponding to the outer diameter of said inner cylindrical portion;
    a coupling cylindrical member having a same outer diameter as the outer diameter of said inner cylindrical portion, said coupling cylindrical member being integrally formed at one end thereof with a coupling portion having an inner diameter corresponding to said outer diameter; and
    cable lead-in openings provided in respective wall surfaces of said inner cylindrical portion and coupling cylindrical member;
    wherein said plurality of annular electrodes are fitted onto outer peripheries of said inner cylindrical portion and coupling cylindrical member one after another at spacings determined by said spacers, and cables are led to said annular electrodes through said cable lead-in openings, and further said inner cylindrical portion is coupled with said coupling cylindrical member to form a multi-stage structure.

6. The electrode rod of claim 4 or 5, wherein said plurality of spacers include a spacer having a mounting portion for mounting a resistance for detecting an electric current on a wall surface thereof.

7. An electrode rod for measuring conductivity or resistivity by supplying an alternating current into a mixed material and measuring a resulting voltage using a group of one resistance and four electrodes, said electrode rod comprising:
    a cylindrical member with a conical distal end;
    four annular electrodes fixed on an outer periphery of said cylindrical member at predetermined spacings; and
    a resistance for detecting an electric current, said resistance being fixed between said annular electrodes.

8. The electrode rod of claim 7, wherein a spacing between second and third annular electrodes of said four annular electrodes is enlarged, and said resistance is fixed between said second and third annular electrodes.

9. The electrode rod of claim 4, 5 or 7, wherein said annular electrodes each have a projection formed on an outer periphery thereof.

* * * * *